(12) United States Patent
Fuhrmann (10) Patent No.: US 9,453,218 B2
(45) Date of Patent: Sep. 27, 2016

(54) METHOD FOR PRODUCING A NUCLEIC ACID LIBRARY HAVING AT LEAST TWO ADJACENT VARIABLE CODON TRIPLETS

(71) Applicant: Markus Fuhrmann, Maxhütte-Haidhof (DE)

(72) Inventor: Markus Fuhrmann, Maxhütte-Haidhof (DE)

( * ) Notice: Subject to any disclaimer, the term of this patent is extended or adjusted under 35 U.S.C. 154(b) by 0 days.

(21) Appl. No.: 14/371,245

(22) PCT Filed: Feb. 14, 2013

(86) PCT No.: PCT/EP2013/053008
§ 371 (c)(1),
(2) Date: Jul. 9, 2014

(87) PCT Pub. No.: WO2013/124211
PCT Pub. Date: Aug. 29, 2013

(65) Prior Publication Data
US 2014/0357531 A1    Dec. 4, 2014

(30) Foreign Application Priority Data
Feb. 20, 2012   (DE) .................. 10 2012 101 347

(51) Int. Cl.
*C12N 15/10*    (2006.01)
*C40B 50/08*    (2006.01)
*C12N 15/66*    (2006.01)

(52) U.S. Cl.
CPC ........... *C12N 15/1093* (2013.01); *C12N 15/10* (2013.01); *C12N 15/66* (2013.01); *C40B 50/08* (2013.01)

(58) Field of Classification Search
None
See application file for complete search history.

(56) References Cited

U.S. PATENT DOCUMENTS

| | | | |
|---|---|---|---|
| 7,695,906 B2 | 4/2010 | Schatz et al. | |
| 8,092,991 B2 | 1/2012 | Schatz et al. | |
| 8,263,335 B2 | 9/2012 | Carr et al. | |
| 2008/0044862 A1 | 2/2008 | Schatz et al. | |
| 2008/0287320 A1* | 11/2008 | Baynes .............. | C12N 15/1027 506/17 |
| 2010/0022410 A1* | 1/2010 | Van den Brulle et al. ..... 506/17 | |

FOREIGN PATENT DOCUMENTS

WO    0075368    12/2000

OTHER PUBLICATIONS

PCT/EP2013/053008—ISR Search Report filed Sep. 4, 2014.

* cited by examiner

*Primary Examiner* — Karen S Weiler
(74) *Attorney, Agent, or Firm* — Simmons Perrine Moyer Bergman PLC (57) ABSTRACT

The invention relates to a method for producing a DNA sequence for a nucleic acid library having a plurality of elements. The synthesized DNA sequence comprises at least three sections. The first section and the third section in each element have defined sequences (D1, D2) that are identical in each element of the nucleic acid library. In a middle second section, at least two adjoining variable codon triplets are arranged.

9 Claims, 6 Drawing Sheets

METHOD FOR PRODUCING A NUCLEIC ACID LIBRARY HAVING AT LEAST TWO ADJACENT VARIABLE CODON TRIPLETS

CLAIM OF PRIORITY

The present application claims the benefit of international application PCT/EP2013/053008, filed on Feb. 14, 2013, which in turn claims the benefit of German application DE 10 2012 101 347.0, filed on Feb. 20, 2012, which in turn has granted as German patent DE 10 2012 101 348 B4, issued on Jan. 16, 2014, all of which are incorporated by reference.

FIELD OF THE INVENTION

The present invention relates to a method for preparing a nucleic acid library comprising at least two adjoining variable codon triplets.

BACKGROUND

DNAs with defined sequences are often required for biomedical research in order to better investigate specific issues. For example, to identify optimized antibodies for specific purposes, gene libraries for antibodies comprising codon triplets for different amino acids at specific key positions are required. Hereby synthetic DNAs are preferred that comprise defined sequence sections and variable sequence sections.

EP 2110435 B1 describes a method for preparing a nucleic acid library comprising a plurality of elements, each element comprising a first, a second and a third nucleotide section. The sequence of the first and the third nucleotide section are identical respectively in the various elements, while the elements of the nucleic acid library differ in the sequence of the second section. The method uses a first at least partially double-stranded oligonucleotide with a single-stranded overhang, the oligonucleotide comprising the sequence of the first or third nucleotide section. The oligonucleotide is connected to an oligonucleotide library. This oligonucleotide library consists of second at least partially double-stranded oligonucleotides each with a complementary overhang. The resulting ligation product is cut and combined with a second oligonucleotide library to a second ligation product. These steps are repeatedly performed until the variable middle part with the desired number of variable codon triplets is fully synthesized. A particular disadvantage of this method is that in each extension step only one codon triplet is added. In addition, each of the first ligation products from the first oligonucleotide library must be combined with each oligonucleotide of the second oligonucleotide library. This requires a lot of equipment and computational effort.

SUMMARY OF THE INVENTION

The object of the invention is to provide a simple, rapid and inexpensive method for the production of nucleic acid libraries with at least two adjoining variable codon triplets, in which the extent of technical equipment is reduced compared to conventional methods.

The above object is achieved by a method comprising the features set out in the claims.

The invention relates to a method for producing a DNA sequence for a nucleic acid library comprising a plurality of elements. The DNA sequence comprises at least three sections. The first and the third section each have defined sequences that are identical in all elements of the nucleic acid library. The invention especially relates to nucleic acid libraries, comprising at least two adjoining variable codon triplets arranged within the second middle section. This is particularly important, for example, in order to specifically investigate the exchange of neighboring amino acids in the active site of proteins.

The method is carried out using at least two oligonucleotide libraries and using at least two substantially complementary single-stranded oligonucleotides or libraries of complementary oligonucleotides with the properties described below:

A first oligonucleotide library consists of oligonucleotides, each oligonucleotide comprising a partial sequence corresponding to the defined first section of the nucleic acid library. Thereafter at least one first variable codon triplet and subsequently a first part of a spacer element and a defined 3' overhang are arranged.

A first complementary oligonucleotide is at least complementary to the oligonucleotides of the first oligonucleotide library. In particular it comprises a partial sequence complementary to the first part of the spacer element of the first oligonucleotide library. Furthermore, the first complementary oligonucleotide comprises at least a first substantially complementary variable codon triplet and a partial sequence complementary to the defined first section of the oligonucleotides of the first oligonucleotide library. The complementary variable codon triplet preferentially consists of three so-called "universal bases" or of a mixture of all four canonical nucleotides. The term "universal bases" is used for nucleotides which can replace any of the four standard nucleotides adenine, cytosine, guanine and thymine without significantly destabilizing adjoining base pair interactions, or without interfering with the biochemical mode of action of the modified oligonucleotides. Oligonucleotides comprising a universal nucleotide can be used without problems as primers in DNA sequencing etc. and they also do not interfere with the enzymatic reactions of polynucleotide kinase, DNA ligase and other enzymes. Such "universal bases" are, for example, known analogues of the canonical bases of the natural nucleic acids that can form complementary base pairs with all natural bases of DNA and RNA. By now synthetic "universal bases" have been produced that form hydrogen bonds with the nucleotides dA, dC, dG or dT without destabilizing the Watson-Crick dsDNA structure. Such familiar "universal bases" include nucleosides of 3-Methyl-7-propinylisocarbostyril (PIM), 3-Methylisocarbostyril (MICS), 5-Methylisocarbostyril (5MICS), 3-Nitropyrrol, 5-Nitroindol and 2'-Desoxyinosine (dI).

A second oligonucleotide library comprises oligonucleotides with a partial sequence forming the second part of the spacer element, at least one second variable codon triplet and a partial sequence corresponding to the defined second section of the nucleic acid library. A second complementary oligonucleotide is substantially complementary to the oligonucleotides of the second oligonucleotide library, each comprising a partial sequence that is complementary to the second section of the oligonucleotides of the second oligonucleotide library, at least a second complementary variable codon triplet, a partial sequence that is complementary to the second part of the spacer element of the oligonucleotides of the further oligonucleotide library and an adjoining defined 3' overhang.

Instead of the described oligonucleotide libraries and corresponding substantially complementary oligonucleotides also a first oligonucleotide library and a second complementary oligonucleotide without a 3' overhang can be used. Instead, two oligonucleotides and two oligonucleotide libraries are used, wherein the first complementary oligonucleotide and the second oligonucleotide library each comprise a 5' overhang.

According to a preferred embodiment of the invention the defined 3' overhangs of the oligonucleotides of the first oligonucleotide library and the second complementary oligonucleotide or the defined 5' overhangs of the oligonucleotides of the second oligonucleotide library and the first complementary oligonucleotide each comprise the same number of nucleotides and are at least substantially complementary to each other.

For the production of the desired nucleic acid with at least two adjoining variable codon triplets the following procedural steps are carried out: First the oligonucleotides of the first oligonucleotide library are each hybridized with the substantially complementary first oligonucleotide. The oligonucleotides of the second oligonucleotide library are each hybridized with the substantially complementary second oligonucleotide. In each case first and second double-stranded DNA libraries are created. These are connected together by ligation via the complementary overhangs of the oligonucleotides of the first oligonucleotide library and the second complementary oligonucleotide, whereby a library of double-stranded DNA ligation products is produced. The DNA ligation products each include the following subsections: a defined first section of the nucleic acid library, at least one first variable codon triplet, a spacer element, at least one second variable codon triplet and a defined second section of the nucleic acid library. By removing the spacer element from the double-stranded DNA ligation products a library of finished double-stranded DNA products is formed. The library of finished double-stranded DNA products each includes the following subsections: a defined first section of the nucleic acid library, at least one first variable codon triplet, at least one second variable codon triplet and a defined second section of the nucleic acid library.

According to a further embodiment of the invention, the above-described oligonucleotides of a first oligonucleotide library are each hybridized with corresponding substantially complementary oligonucleotides of a first complementary oligonucleotide library. The oligonucleotides of the first complementary oligonucleotide library each comprising the following partial sequences: a first partial sequence complementary to the first part of the spacer element of the first oligonucleotide library, a codon triplet complementary to one of the oligonucleotides from the first oligonucleotide library and a partial sequences complementary to the defined first section of the oligonucleotides of the first oligonucleotide library. For each oligonucleotide of the first oligonucleotide library a substantially complementary oligonucleotide is available in the first complementary oligonucleotide library. The respective oligonucleotides are each referred to as just substantially complementary due to the above described 3' or 5' overhang. As described above, the oligonucleotides of the first oligonucleotide library preferably have a complementary 3' overhang with respect to the respective complementary oligonucleotides of the second complementary oligonucleotide library. Alternatively, the oligonucleotides of the first complementary oligonucleotide library comprise a 5' overhang in respect to the oligonucleotides of the first oligonucleotide library.

In this embodiment, two oligonucleotides are hybridized to one another that are complementary apart from the overhangs. This is particularly advantageous when only a few different codon triplets need to be tested. The respective hybridized oligonucleotides form the first double-stranded DNA library. Instead of the so-called second complementary oligonucleotide a second complementary oligonucleotide library can be used in analogy.

According to an embodiment of the invention, the oligonucleotides of the first oligonucleotide library and the second complementary oligonucleotide each comprise defined respectively complementary 3' overhangs and the first complementary oligonucleotide and the oligonucleotides of the second oligonucleotide library also each comprise defined 3' overhangs. Preferably, these 3' overhangs are of different lengths and not complementary to one another. In particular, the 3' overhangs of the first complementary oligonucleotide and the 3' overhangs of the oligonucleotides of the second oligonucleotide library are each different in length and not complementary to the defined 3' overhangs of the oligonucleotides of the first oligonucleotide library and the second complementary oligonucleotide. The different designs of the 3' overhangs of the oligonucleotides or oligonucleotide libraries ensure a correct alignment thereof during hybridization and subsequent ligation.

According to a further embodiment of the invention the oligonucleotides each comprise defined 5' overhangs. Preferably, the 5' overhangs of the oligonucleotides of the second oligonucleotide library and the first complementary oligonucleotide each have the same length and are complementary to one another. Meanwhile the 5' overhangs of the second complementary oligonucleotide and the 5' overhangs of the oligonucleotides of the first oligonucleotide library each vary in length and are not complementary to one another. The different design of the 5' overhangs of the oligonucleotides or oligonucleotide libraries ensures correct alignment of the oligonucleotides during hybridization and subsequent ligation.

The spacer element comprises at least one recognition site for at least one type IIS restriction endonuclease. According to a preferred embodiment the spacer element comprises two recognition sites for at least one, preferably two, type IIS restriction endonucleases. Type IIS restriction endonucleases recognize the DNA to be cut at the respective specific recognition site and then they cut the DNA at a restriction site located at a defined distance from the recognition site. Said spacer element is selected such that the at least one type IIS restriction endonuclease cuts the double-stranded DNA ligation product 3' after the third nucleotide of the first variable codon triplet and/or 5' upstream of the first nucleotide of the second variable codon triplet. Thus, the spacer element can easily be cut out of the DNA ligation product.

According to one embodiment a type IIS restriction endonuclease is used that cuts the DNA "blunt", that is the restriction endonuclease cuts the DNA without producing overhangs. After religation of the cut ligation product a DNA sequence with the following sequence is obtained: a defined first section of the nucleic acid library, at least one first variable codon triplet, at least one second variable codon triplet and a defined second section of the nucleic acid library. When using a type IIS restriction endonuclease that generates 3' or 5' overhangs during cutting, those overhangs need to be replenished or degraded to blunt ends by standard processes. For this purpose Klenow polymerase, T4 DNA polymerase, etc. can be used. After religation of the cut and smoothed ligation product a DNA with the sequence described above is obtained.

Furthermore it may be provided that the oligonucleotides of the first oligonucleotide library each comprise two adjoining or substantially adjoining variable codon triplets and/or that the oligonucleotides of the second oligonucleotide library also comprises two adjoining or substantially adjoining variable codon triplets. Accordingly, the first and/or the second complementary oligonucleotide each have two adjoining or substantially adjoining complementary variable codon triplets each comprising three "universal bases". As described above, complementary oligonucleotide libraries can be used instead of the first and/or second complementary oligonucleotide. With the method described above a nucleic acid sequence with three or four adjoining or substantially adjoining variable codon triplets can now be constructed.

When selecting the oligonucleotides the use of other modifications is possible, for example, modification wherein the oligonucleotides are each constructed in such a way that after hybridization and ligation the corresponding double-stranded DNA ligation product is formed. For example, the first oligonucleotide library can consist of two oligonucleotides, wherein the first oligonucleotide comprises the following partial sequence: 5'—a defined first section D1—a first variable codon triplet TV1-1$x$ and wherein the second oligonucleotide comprises the following partial sequence: a second variable codon triplet TV1-1$y$—a first partial sequence S1 of a spacer element S and a defined substantially complementary 3' overhang U1. The first complementary oligonucleotide or the first complementary oligonucleotide library accordingly comprises the following partial sequence: 5'—a complementary partial sequence—a second substantially complementary variable codon triplet—a first substantially complementary variable codon triplet—a sequence complementary to the defined sequence—a defined 3' overhang. After hybridization and ligation of the three oligonucleotides a DNA ligation products with the following sequence is produced: a defined first section—a first variable codon triplet—a second variable codon triplet—a first partial sequence S1 of a spacer element. The described procedural steps are preferably not carried out with linear DNA fragments but in each case in a suitable cloning vector. Specifically, the library of double-stranded DNA ligation product still containing the spacer element between the at least two variable codon triplets, is integrated via ligation into an appropriately prepared cloning vector using the defined 3' overhang of the first complementary oligonucleotide and the defined 3' overhangs of the second oligonucleotide library. The resulting ligation product vectors are treated with at least one type IIS restriction endonuclease, wherein said spacer element is excised. The library of cut ligation product vector is then recyclized by religation to a product vector library.

Nucleic acid sequences with an arbitrary number of adjoining variable codon triplets can be generated by combinations of a plurality of suitably designed libraries of the first, second, etc. product vectors containing sequences for additional spacer elements instead of the defined first and second sections of the nucleic acid library. According to one embodiment a first library of product vector with a first variable nucleic acid section comprises at least two different selection markers. A second library of product vector with a second variable nucleic acid section comprises at least two different selection markers. The two product vector libraries are each cut at two locations using appropriate restriction endonucleases. The resulting fragments are newly combined and joined by religation. The resulting new product vectors comprise, for example, twice the first variable nucleic acid section, twice the second variable nucleic acid section, the combination of nucleic acid section one and nucleic acid section two or the combination of nucleic acid section two-and nucleic acid section one. The product vectors with the desired nucleic acid combination can be identified by a specific double selection based on the selectable markers.

The advantages of the method according to the invention are, in particular, that the method can be automated easily. The number of necessary procedural steps is substantially reduced compared to the above-described method according to the prior art. In addition, less oligonucleotides are required, which in turn reduces the cost of the method. The described method uses libraries consisting of hybridized oligonucleotides; the hybridized oligonucleotides of the libraries are joined together, whereby the hybridized oligonucleotides each have at least one overhang that cannot be found in the nucleic acid library product after the removal of the central spacer element. The sections forming the overhang of the single stranded oligonucleotides are subsequently removed and are therefore not part of the final product. Therefore optimized overhangs can be used for the hybridization and ligation reaction. In particular, the overhangs do not have to be varied according to the desired mutation. This reduces the process costs and improves the quality of the resulting final product.

For this method, 82 oligonucleotides in total (4·20+2) have to be provided as mixture for the preparation of four successive positions with a mutation rate of 20 variations. Thus, compared to conventionally known methods less starting oligonucleotides are required, thereby effectively reducing the costs for this method. Furthermore, the working load for pipetting and therefore the required working time are significantly reduced. Moreover, in the described method the hybridization and ligation reactions can be performed in parallel, therefore multiple processes may be performed at the same time. Only the removal reactions have to be performed sequentially. Assuming saturating high enzyme and coenzyme concentrations, these reactions are (quasi-) unimolecular and thus only dependent on the concentration of the substrate. After the religation reaction the substrate can be reproduced by cloning in almost any amount.

BRIEF DESCRIPTION OF THE DRAWINGS

The following examples are intended to illustrate the invention and its advantages with reference to the accompanying figures. The size ratios of the individual elements in the figures do not always match the real size ratios. It is to be understood that in some instances various aspects of the invention may be shown exaggerated or enlarged to facilitate an understanding of the invention.

DETAILED DESCRIPTION

The same or equivalent elements of the invention are designated by identical reference characters. Furthermore and for the sake of clarity, only the reference characters relevant for describing the respective figure are provided. It should be understood that the embodiments described are only examples of the method according to the invention and they are not intended to limit the scope of the disclosure.

Figure 1:
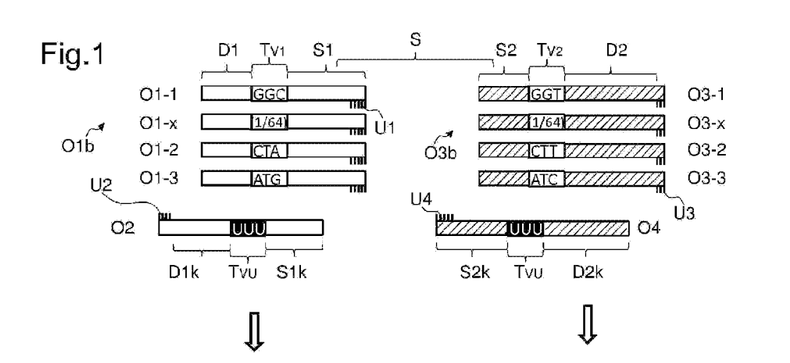
FIGS. 1 through 11 illustrate the preparation of a nucleic acid library with two adjoining variable codon triplets.

FIGS. 1 through 11 illustrate the preparation of a nucleic acid library with two adjoining variable codon triplets TV1 and TV2. FIG. 1 shows the different oligonucleotides O2 and O4 and oligonucleotide libraries O1b and O3b which are used in the method according to the invention. A first oligonucleotide library O1b comprises first oligonucleotides O1-x with four defined subsections. A first partial sequence D1 corresponds to the first defined section of the nucleic acid library. A first variable codon triplet TV1 is located immediately downstream. The number of different oligonucleotides O1-x with different codon triplets used in the method depends on which different amino acids need to be expressed. In extreme cases, sixty-four different oligonucleotides O1-x are used to cover the whole possible spectrum of amino acids and premature discontinuations of the protein chain by stop codons. Following the variable codon triplet TV1a first partial sequence S1 of a spacer element S is arranged. In addition, the oligonucleotides O1-x of the first oligonucleotide library O1b each comprise a defined 3' overhang U1 consisting of five nucleotides.

The second oligonucleotide O2 is constructed substantially complementary to the oligonucleotides O1-x of the first oligonucleotide library O1b. It comprises a partial sequence S1k complementary to the first partial sequence S1 of the spacer S of the first oligonucleotides O1-x. Immediately downstream a first variable codon triplet TVU is arranged comprising three "universal bases" (see description) and subsequently a partial sequence D1k complementary to the first section D1 of the first oligonucleotides O1-x is arranged. Furthermore, the second oligonucleotide O2 comprises a four nucleotide overhang U2 at its 3' end. This preferably corresponds to an overhang that is produced naturally when DNA is cut with certain restriction enzymes.

A second oligonucleotide library O3b includes third oligonucleotides O3-x each comprising four defined subsections. A first partial sequence forms the second partial sequence S2 of the spacer element S. Immediately downstream a second variable codon triplet TV2 and a partial sequence are arranged, wherein the partial sequence corresponds to the defined second section D2 of the nucleic acid library. As in the case of the oligonucleotides O1-x of the first oligonucleotide library O1b, a number of different third oligonucleotides O3-x is used, depending on the amino acids that should be expressed. Furthermore, the oligonucleotides O3-x of the second oligonucleotide library O3b comprise a three nucleotide overhang U3 at the 3' end. This overhang preferably corresponds to an overhang that is produced naturally when DNA is cut with certain restriction enzymes.

Further, a fourth oligonucleotide O4 is shown, which is substantially complementary to the oligonucleotides O3-x of the second oligonucleotide library O3b. It comprises a partial sequence D2k complementary to the second section D2 of the third oligonucleotides O3-x. Immediately downstream a second variable codon triplet TVU comprising three "universal bases" and subsequently a partial sequence S2k complementary to the second partial sequence S2 of the spacer element S of the third oligonucleotide O3 are arranged. Furthermore, the oligonucleotide O4 comprises a 3' overhang U4 made of five nucleotides complementary to the 3' overhangs of the first oligonucleotides O1-x.

Figure 2:
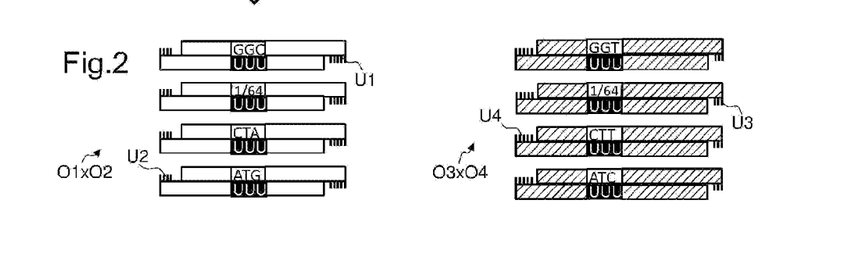
Figure 3:
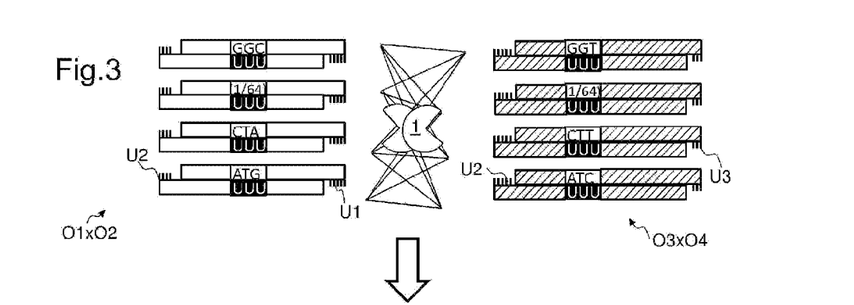

In a first procedural step, the oligonucleotides O1-1, O1-2, O1-3 and O1-X of the first oligonucleotide library O1b are hybridized respectively with the second oligonucleotide O2. An oligonucleotide 1-x/oligonucleotide 2—mixture is first heated up to 95° C. and is then cooled down slowly. Accordingly, the third oligonucleotides O3-1, O3-2, O3-3 and O3-x are hybridized respectively with the fourth oligonucleotide O4. The resulting double-stranded O1×O2 DNA product libraries or O3×O4 DNA product libraries are schematically shown in FIG. 2.

Figure 4:
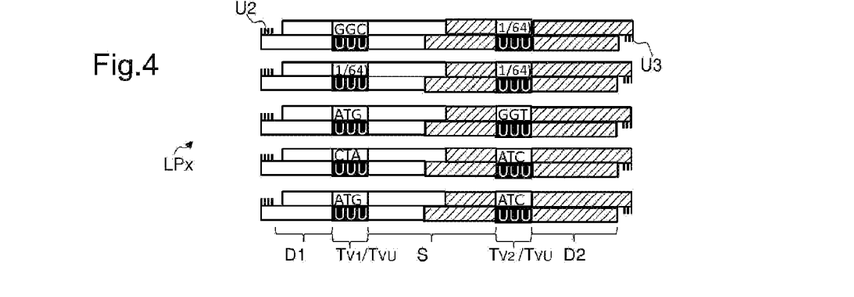
Figure 5:
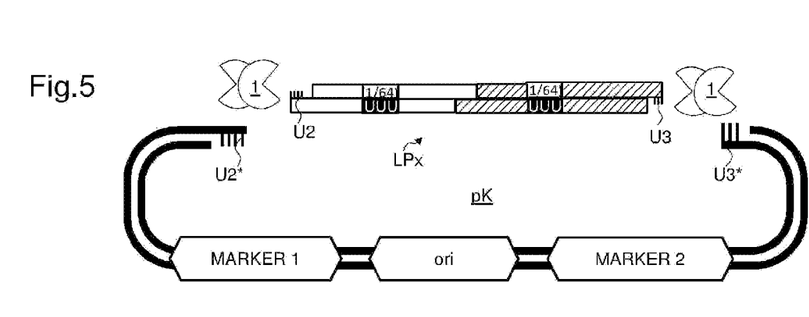

In a second procedural step (see FIG. 3), the oligonucleotide 1-x/oligonucleotide 2-DNAs O1×O2 are connected to the oligonucleotide 3-x/oligonucleotide 4-DNAs O3×O4 via the complementary overhangs U1 and U4 of the oligonucleotides 1 and 4 using a ligase 1. Some of the resulting double-stranded ligation products LPx are shown in FIG. 4. The ligation products LPx products each comprise the following subsections: a defined first section D1 of the nucleic acid library, a first variable codon triplet TV1, a spacer element S, a second variable codon triplet TV2 and a defined second section D2 of the nucleic acid library.

Figure 6:
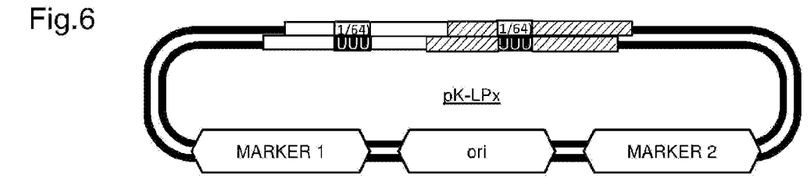

The double-stranded DNA ligation product LPx has the defined 3' overhangs U2 and U3 of the second and third oligonucleotides of O2, O3-x. A cloning vector pK is prepared by cutting, for example, with two restriction endonucleases and dephosphorylation (see FIG. 5). The restriction endonucleases are specifically selected to produce overhangs U2* and U3* corresponding to the defined overhangs U2, U3 of the ligation products LPx. Subsequently, the ligation products LPx are integrated into the prepared cloning vector pK using ligase 1, thereby creating a library of ligation product vectors pK-LPx (FIG. 6).

Figure 7:
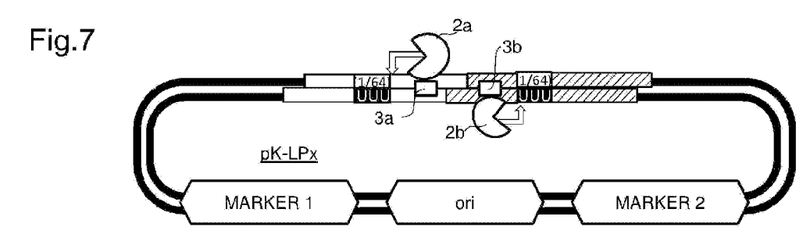
Figure 8:
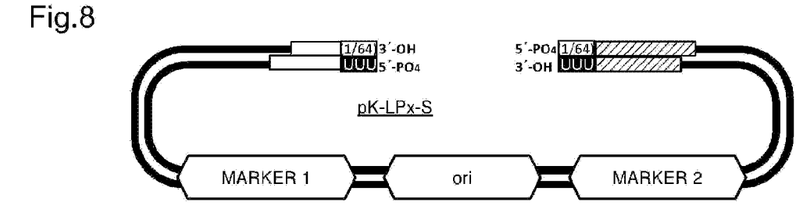
Figure 9:
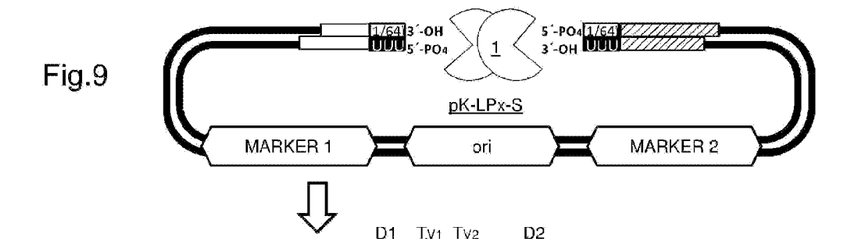
Figure 10:
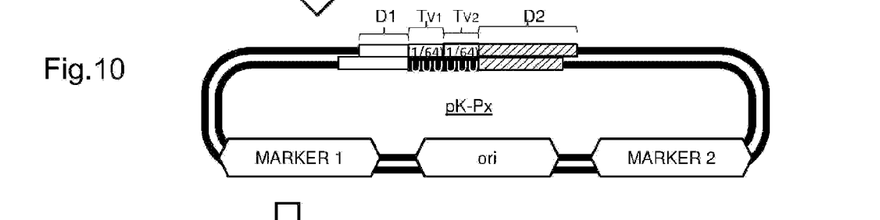

The spacer element S of the ligation products LPx comprises at least one, preferably two, recognition sites 3a, 3b for at least one type IIS restriction endonuclease 2a, 2b (see FIG. 7). Type IIS restriction endonucleases cut DNA "blunt", that is without creating an overhang, at a site that has a defined distance from the recognition site 3a, 3b. The recognition sites 3a, 3b for the type IIS restriction endonucleases 2a, 2b are arranged within the spacer element S in such a way that the first restriction endonuclease 2a cuts directly after the first variable codon triplet TV1 and that the second restriction endonuclease 2b cuts directly before the second codon triplet TV2. Thereby the spacer element S is completely excised from the ligation product vector pK-LPx. A linear fragment pK-LPx-S is formed, which consists of cloning vector and ligation product LPx minus spacer element S (see FIG. 8). The linear fragment pK-LPx-S is religated by means of a ligase 1 thereby producing a product vector pK-Px (see FIGS. 9 and 10). The product vector pK-Px now contains the desired DNA fragment with the following subsections: a defined first section D1 of the nucleic acid library, a first variable codon triplet TV1, a second variable codon triplet TV2 and a defined second section D2 of the nucleic acid library.

Figure 11:
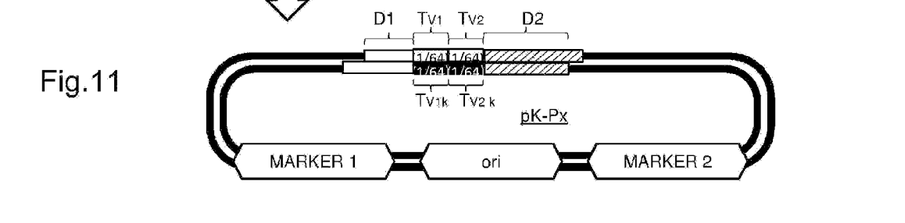

As shown in FIG. 11, the universal nucleotides are replaced by "standard" nucleotides A, T, C and G in a last procedural step. This is possible using conventionally known cloning methods, for example, so-called nick replication, rolling circle, PCR or similar methods. Another simple way is to duplicate the plasmid in a suitable host, such as E. coli. Thereby the universal nucleotides of the variable codon triplets TVU are replaced with the complementary "normal" nucleotides A, T, C and G by the repair machinery of the host, thus generating the complementary variable codon triplets TV1k and TV2k.

Figure 12:
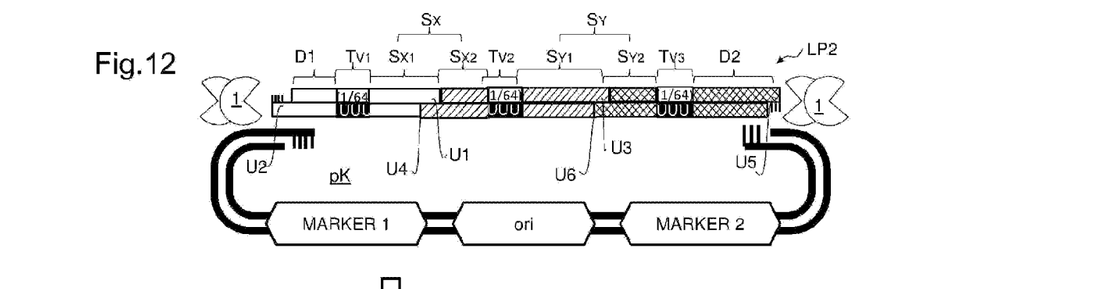
FIGS. 12 through 16 show the preparation of a nucleic acid library with three adjoining variable codon triplets.

FIGS. 12 through 16 show the preparation of a nucleic acid with three adjoining variable codon triplets. The six oligonucleotides used therein are listed in tabular form:

O1x    Oligonucleotide library:
      5' - a defined first section D1 - a first variable codon triplet -continued

| | |
|---|---|
| | TV1 - a first partial sequence SX1 of a spacer element SX - a defined 3' overhang U1 |
| O2 | 5' - a complementary partial sequence SX1k - a codon triplet TVU - a complementary sequence D1k - a defined 3' overhang U2 |
| O3x | Oligonucleotide library: 5' - a second partial sequence SX2 of a spacer element SX - a second variable codon triplet TV2 - a first partial sequence SY1 of a spacer element SY - a defined 3' overhang U3 |
| O4 | 5' - a complementary partial sequence SY1k - a codon triplet TVU - a complementary partial sequence SX2k - a defined 3' overhang U4 |
| O5x | Oligonucleotide library: 5' - a second partial sequence SY2 of a spacer element SY - a third variable codon triplet TV3 - a defined second section D2 - a defined 3' overhang U5 |
| O6 | 5' - a complementary sequence D2k - a codon triplet TVU - a complementary partial sequence SY2k - a defined 3' overhang U6 |

For the defined overhangs the following is true: U1 is complementary to U4; U3 is complementary to U6; U2 and U5 are complementary to the overhangs of a cloning vector pK produced by restriction. These overhangs can be prepared, for example, with an incomplete PCR, ligation, independent cloning with appropriate polymerases, etc.

The oligonucleotides or oligonucleotide libraries O1x and O2, O3X and O4 as well as O5x and O6 are each hybridized to one another. Subsequently the oligonucleotide 1/oligonucleotide 2 DNAs O1×O2 are connected to the oligonucleotide 3/oligonucleotide 4 DNAs O3×O4 and the oligonucleotide 5/oligonucleotide 6 DNAs O5×O6 using ligase 1. Thereby a library of double-stranded ligation product LP2 is formed (FIG. 12). The ligation products LP2 each include the following subsections: a defined first section D1 of the nucleic acid library, a first variable codon triplet TV1, a first spacer element SX, a second variable codon triplet TV2, a second spacer element SY, a third variable codon triplet TV3 and a defined second section D2 of the nucleic acid library.

Figure 13:
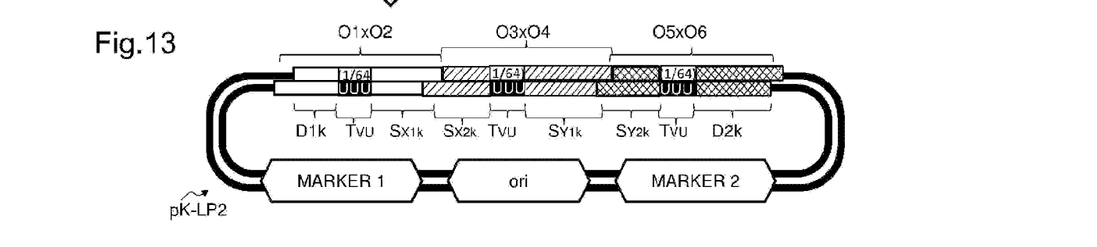

The ligation products LP2 are integrated into a suitably prepared cloning vector pK using the overhangs U2 and U5, thereby generating ligation product vectors pK-LP2 (FIG. 13). The spacer elements SX and SY of the ligation products LP2 each comprise at least one, preferably two, recognition sites 3a-3d for at least one type IIS restriction endonuclease 2a-2d (see FIG. 14 and FIG. 15). The recognition sequences 3a-3d for the type IIS restriction endonucleases 2a-2d are disposed within the spacer elements SX and SY in such a way that a restriction endonuclease 2a, 2c cuts right after the first variable codon triplet TV1 or directly after the second variable codon triplet TV2 and the other restriction endonuclease 2b, 2d cuts directly in front of the second or third codon triplet TV2, TV3. Thereby the spacer elements SX and SY can be cut out of the ligation product vectors pK-LP2 in two successive procedural steps. Hereby it is important that the spacer elements SX and SY each have different recognition sites 3a through 3d for the restriction endonucleases 2a through 2d. Thereby first one spacer element SX or SY and subsequently the other spacer element SY or SX is removed in a targeted manner.

Figure 14:
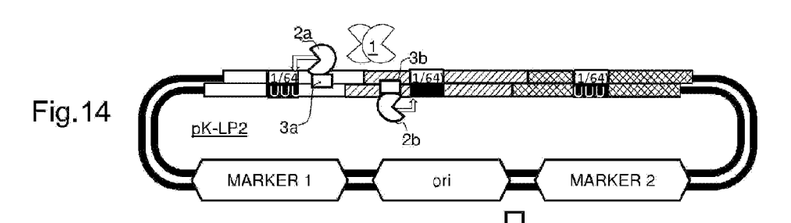
Figure 15:
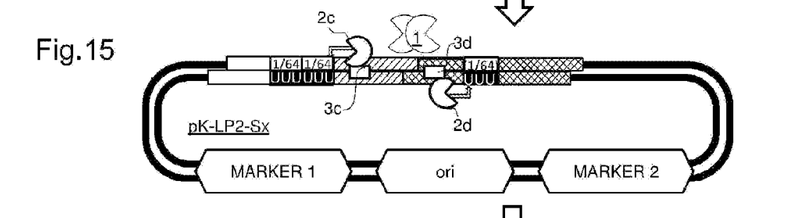
Figure 16:
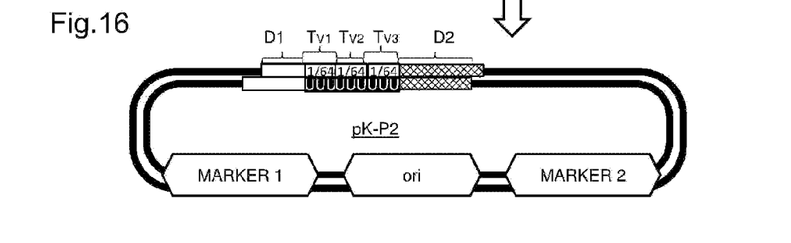

FIG. 14 shows the excision of the spacer element SX from the ligation product vectors pK-LP2 using the type IIS restriction endonucleases 2a and 2b before the excision of the spacer element SY. The cut vector is religated into the vector pK-LP2-Sx (see FIG. 15). The second spacer element SY is then cut out from the vector pK-LP2-Sx using two different type IIS restriction endonucleases 2c and 2d. After religation with ligase 1 the product vector pK-P2 with the desired DNA fragment is obtained. This includes in particular three consecutively adjoining variable codon triplets. The DNA fragment contained in the product vector pK-P2 comprises the following sections: a defined first section D1 of the nucleic acid library, a first variable codon triplet TV1, a second variable codon triplet TV2, a third variable codon triplet TV3 and a defined second section D2 of the nucleic acid library (FIG. 16). Similar to FIG. 11, the universal nucleotides in the product vector pK-P2 are replaced by "normal" nucleotides in a last procedural step (not shown).

Figure 17:
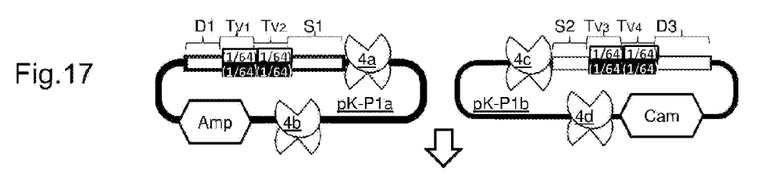
FIGS. 17 through 21 show the preparation of a nucleic acid library with four adjoining variable codon triplets.
Figures 20, 21:
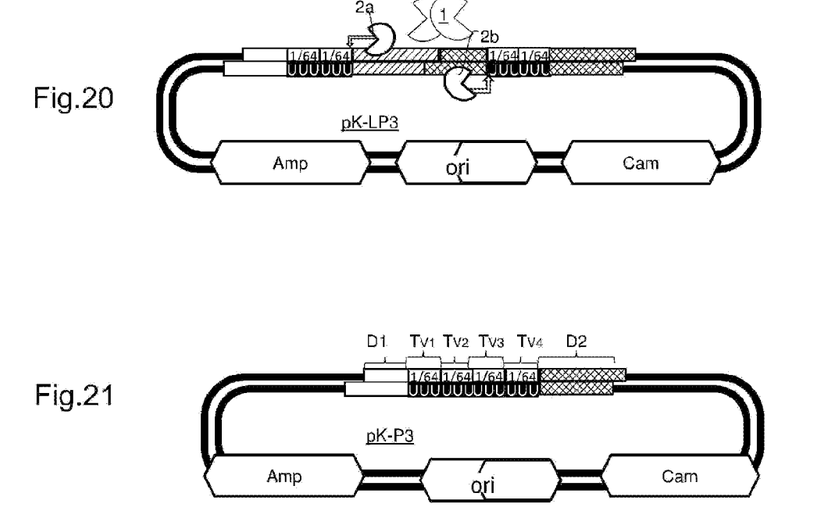

FIGS. 17 through 21 show a way of connecting two libraries of DNA fragments generated according to the invention to form a library of a large DNA fragment comprising the following sequence: a defined first section D1 of the nucleic acid library, a first variable codon triplet TV1, a second variable codon triplet TV2, a third variable codon triplet TV3, a fourth variable codon triplet TV4 and a defined second section D2 of the nucleic acid library (FIG. 21). First two libraries pK-P1a and pK-P1b, each with any two adjoining variable codon triplets, are generated in accordance with the procedural steps described in FIGS. 1 through 11, wherein:

pK-P1a comprises a defined first section D1 of the nucleic acid library, a first variable codon triplet TV1, a second variable codon triplet TV2 and a first partial sequence S1 of a spacer element S and wherein pK-P1b comprises a second partial sequence S2 of a spacer element S, a third variable codon triplet TV3, a fourth variable codon triplet TV4 and a defined second section D2 of the nucleic acid library.

The starting plasmids of the first library pK-P1a each comprise at least one first resistance marker gene MARKER 1, for example, an ampicillin (Amp)-resistance. The starting plasmids of the second library pK-P1b each comprise at least one second resistance marker gene MARKER 2, for example, a Cam-resistance. The vectors of the first library pK-P1a are cut with two restriction endonuclease 4a and 4b, wherein the first restriction endonuclease 4a preferably cuts blunt after the last nucleotide of the first partial sequence S1 of the spacer element S. In addition, the vectors of the first library pK-P1a are cut with a second restriction endonuclease 4b in the origin of replication. This produces the fragment library F(pK-P1a) comprising the above-mentioned first DNA fragment and the first resistance marker gene Amp. The vectors of the second library pK-P1b are preferably cut blunt with a third restriction endonuclease 4c in front of the first nucleotide of the second partial sequence S2 of the spacer element S. In addition, the vectors of the second library pK-P1b are cut with a fourth restriction endonuclease 4d in the origin of replication. This produces the fragment library F(pK-P1b) comprising the above mentioned second DNA fragment and the second resistance marker gene Cam. Preferably the same restriction endonucleases 4b, 4d are used to cut the vectors pK-P1a and pK-P1b in the origin of replication respectively, that is restriction endonuclease 4b=restriction endonuclease 4d.

Figure 18:
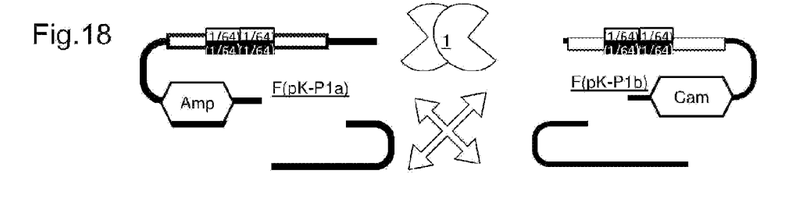
Figure 19:
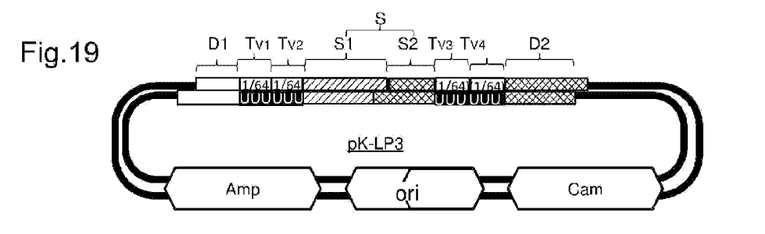

Both fragment libraries F(pK-P1a) and F(pK-P1b) are then connected to one another using ligase 1 (FIG. 18). This creates a library of ligation product vector pK-LP3 (FIG. 19). It comprises a DNA sequence consisting of a defined first section D1 of the nucleic acid library, a first variable codon triplet TV1, a second variable codon triplet TV2, spacer-sequence S, a third variable codon triplet TV3, a fourth variable codon triplet TV4 and a defined second section D2 of the nucleic acid library as well as the two resistance marker genes Amp and Cam. The partial fragments of the origin of replication resulting from the restriction with the restriction endonucleases 4b, 4d are joined via ligation to a functional origin of replication. The ligation product vectors pK-LP3 can be selected specifically using double selection on Amp and Cam. Since the ligation product vectors pK-LP3 comprise a functional origin of replication, they can be replicated easily in a suitable organism, such as E. coli.

The spacer element S is then removed from the ligation product vectors pK-LP3 using type IIS restriction endonucleases 2a, 2b and religation with ligase 1 (FIG. 20). Thereby the product vectors pK-P3 containing the desired DNA sequence are formed (FIG. 21).

Alternatively, four oligonucleotides O5b, O6, O7b and O8 (see table) can also be used in a method according to FIGS. 1 through 11, each oligonucleotide directly including two adjoining variable codon triplets, that is

| | |
|---|---|
| O5b | 5' - a defined first section D1 - a first variable codon triplet TV1 - a second variable codon triplet TV2 - a first partial sequence S1 of a spacer element S - a defined 3' overhang U5 |
| O6 | 5' - a complementary partial sequence S1k - a codon triplet TVU - a codon triplet TVU - a complementary sequence D1k - a defined 3' overhang U6 |
| O7b | 5' - a second partial sequence S2 of a spacer element SX - a third variable codon triplet TV3 - a fourth variable codon triplet TV4 - a defined second section D2 - a defined 3' overhang U7 |
| O8 | 5' - a complementary sequence D2k - a codon triplet TVU - a codon triplet TVU - a complementary partial sequence S2k - a defined 3' overhang U8 |

This directly produces a product library comprising the desired DNA sequence corresponding to FIG. 21.

Figure 22:
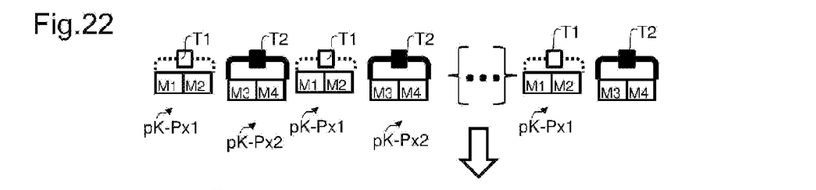
FIGS. 22 through 24 show the production of nucleic acid libraries with a plurality of adjoining variable codon triplets.
Figure 23:
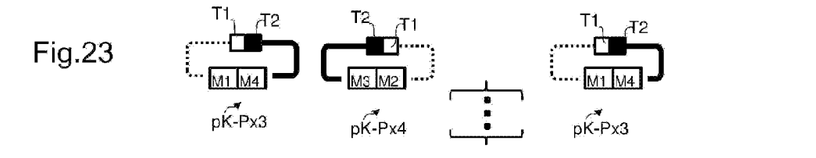
Figure 24:
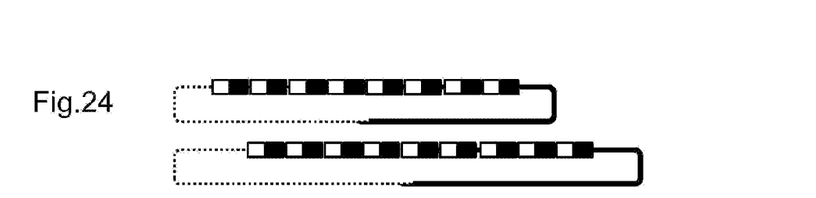

FIGS. 22 through 24 schematically show the generation of nucleic acid libraries in which a plurality of variable codon triplets is arranged next to each other. This is done by combinations of several libraries of correspondingly constructed product vectors pK-Px1, pK-Px2, each containing sequences for additional spacer elements instead of the defined first and second sections of the nucleic acid library. In particular, the use of several different marker genes M1-M4 is necessary and useful.

By combinations of several suitably designed libraries of first, second, etc. product vectors pK-PX1, pK-Px2 with sequences for additional spacer elements instead of the defined first and second sections of the nucleic acid library, nucleic acid sequences with an arbitrary number of adjoining variable codon triplets can thus be generated. According to one embodiment a first library of product vector pK-Px1 with a first variable nucleic acid section comprises at least two different selection markers M1 and M2. A second library of product vector pK-Px2 with a second variable nucleic acid section comprises at least two further different selection markers M3 and M4. The two product libraries pK-Px1, pK-Px2 are each cut at two locations by means of suitable restriction endonucleases and the resulting fragments are recombined by religation (see FIGS. 17 through 21). Thereby libraries of product-vectors (see FIG. 23) are produced comprising, for example, two times the first variable nucleic acid section, two times the second variable nucleic acid section, a combination of nucleic acid section one and nucleic acid section two (=library pK-Px3) or a combination of nucleic acid section two and nucleic acid section one (=library pK-Px4). The libraries with the desired nucleic acid combination can be selected specifically and identified based on the selection marker M1-M4. For example, the product library pK-Px1 can be selected by double selection on marker M1 and marker M2 and product library pK-Px2 can be selected by double selection on marker M3 and marker M4.

Nucleic acid libraries with a plurality of adjoining variable codon triplets can thus be constructed by further combinations (FIG. 24).

Figure 25:
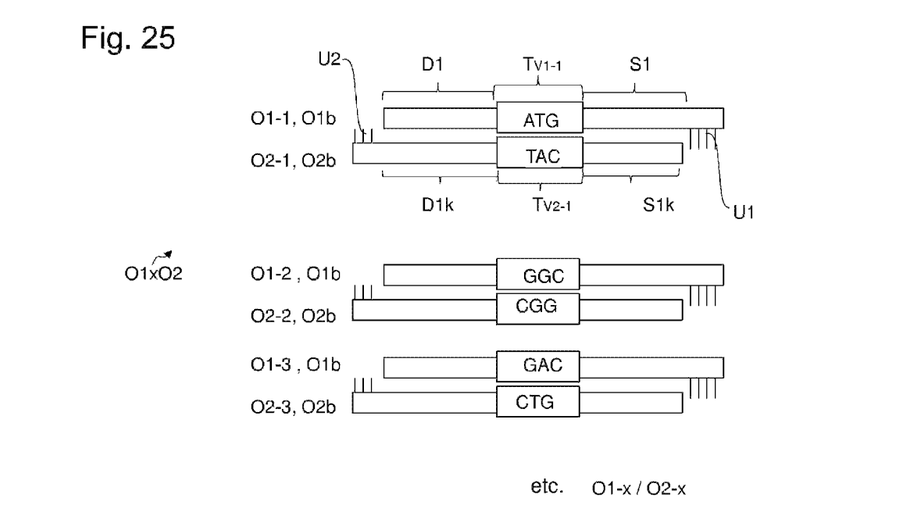
FIG. 25 shows a further embodiment of the oligonucleotides used in the method according to the invention.

FIG. 25 shows a further embodiment of the oligonucleotides used in the method according to the invention. Here, the above-described oligonucleotides O1-1 through O1-x of a first oligonucleotide library O1b are hybridized respectively with the corresponding substantially complementary oligonucleotides O2-1 through O2-x of a first complementary oligonucleotide library O2b. The oligonucleotides O2-1 through O2-x of the first complementary oligonucleotide library O2b each comprise the following partial sequences: a first partial sequence S1k complementary to the first partial sequence S1 of the spacer element S (see FIG. 1) of a first oligonucleotide library O1b, a codon triplet TV2-1 through TV2-x complementary to one of the oligonucleotides O1-1 through O1-x of the first oligonucleotide library O1b and a partial sequence D1k complementary to the defined first section D1 of the oligonucleotides O1-1 through O1-x of the first oligonucleotide library O1b. For each oligonucleotide O1-1 through O1-x of the first library O1b a substantially complementary oligonucleotide O2-1 through O2-x is available in the first complementary oligonucleotide library O2b. Oligonucleotides O1-x and O2-x are each described as only being substantially complementary, because at least the oligonucleotides O1-x of the first oligonucleotide library O1b comprise a 3' overhang U1 with respect to the respective complementary oligonucleotides O2-x of the first complementary oligonucleotide library O2b. Furthermore, the oligonucleotides O2-x of the first complementary oligonucleotide library O2b preferably have a 3' overhang with respect to the respective complementary oligonucleotides O1-x of the first oligonucleotide library O1b.

In this embodiment, two oligonucleotides O1-x and O2-x are hybridized to each other that are mostly complementary and only differ because of their 3' overhangs. This is particularly advantageous when only a few different codon triplets need to be tested. The multitude of different hybridized oligonucleotides O1-x/O2-x form the first double-stranded DNA library O1×O2. Instead of the so-called second complementary oligonucleotide O4 (see FIGS. 1 through 11) a second complementary oligonucleotide library O4b (not shown) may be used in analogy.

Figure 26:
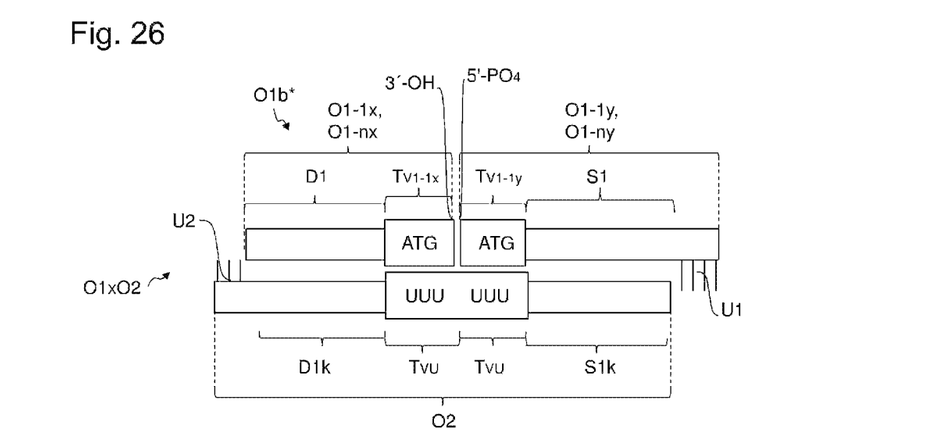
FIG. 26 shows a further embodiment of the oligonucleotides used in the method according to the invention.

FIG. 26 shows a further embodiment of the oligonucleotides used in the method according to the invention, wherein the starting oligonucleotides already include two adjoining variable codon triplets. Hereby it is provided that the first oligonucleotide library O1b* consist of two oligonucleotides O1-1x through O1-nx and O1-1y through O1-ny, wherein the first oligonucleotide O1-1x comprises the following partial sequences: 5'—a defined first section D1-a first variable codon triplet TV1-1x and wherein the second oligonucleotide O1-1y comprises the following partial sequences: a second variable codon triplet TV1-1y-a first partial sequence S1 of a spacer element S and a defined 3' overhang U1. Accordingly, the first complementary oligonucleotide O2 comprises the following partial sequences: 5'-a complementary partial sequence S1k—a codon triplet TVU—a codon triplet TVU—a complementary sequence D1k—a defined 3' overhang U2. DNA ligation products are created by hybridization and ligation of the three oligonucleotides O1-nx, O1-ny and O2, the DNA ligation products comprising the following sequence: a defined first section D1—a first variable codon triplet TV1-1x—a second variable codon triplet TV1-1y—a first partial sequence S1 of a spacer element S. These are used for example in a method according to FIGS. 17 through 19.

The invention has been described with reference to preferred embodiments. To the expert it is also conceivable, however, to make changes and modifications without leaving the scope of protection of the appended claims. In particular the invention shall also encompass the use of modified oligonucleotides that form corresponding double-stranded DNA molecules after hybridization and ligation.

LIST OF REFERENCE NUMBERS 1 ligase
2 type IIS restriction endonuclease
3 recognition site
4 restriction endonuclease
D defined section
A nucleotide adenine
Amp ampicillin resistance gene
C nucleotide cytosine
Cam cam (Chloramphenicol) resistance gene
F fragment
G nucleotide guanine
LP ligation product
ori origin of replication
O oligonucleotide
Ob oligonucleotide library
O1×O2 ligation product library
P product
pK cloning vector
pK-LP ligation product vector
pK-P product vector
S spacer element
T nucleotide thymine
TV variable codon triplet
U universal nucleotide
U1-U4 3' overhang
U2*, U3* 3' overhang

The invention claimed is:

1. A method for producing a DNA sequence for a nucleic acid library comprising a plurality of elements,
wherein the DNA sequence comprises at least three sections,
wherein the first and the third sections in each element have defined sequences that are identical in each element of the nucleic acid library,
wherein a central second section comprises at least two adjoining variable codon triplets,
wherein at least two oligonucleotide libraries and at least two single stranded oligonucleotides with the following characteristics are used in this method:
  a first oligonucleotide library consisting of oligonucleotides each comprising a partial sequence corresponding to the defined first section of the nucleic acid library, at least one first variable codon triplet, a subsequently arranged first partial sequence of a spacer element and a defined 3' overhang;
  a first complementary oligonucleotide which may be a member of a library of first complementary oligonucleotides, each member comprising at least one codon triplet complementary to that of one of the oligonucleotides from the first oligonucleotide library, wherein the first complementary oligonucleotide is complementary to the oligonucleotides of the first oligonucleotide library, and comprises a partial sequence that is complementary to the first partial sequence of the spacer element of the oligonucleotides of the first oligonucleotide library, at least one first complementary variable codon triplet and a partial sequence-complementary to the defined first section of the oligonucleotides of the first oligonucleotide library;
  a second oligonucleotide library consisting of oligonucleotides each comprising a partial sequence forming the second partial sequence of the spacer element, at least one second variable codon triplet and a partial sequence corresponding to the defined third section of the nucleic acid library; and
  a second complementary oligonucleotide which may be a member of a library of second complementary oligonucleotides, each member comprising at least one codon triplet complementary to that of one of the oligonucleotides from the second oligonucleotide library, wherein the second complementary oligonucleotide is complementary to the oligonucleotides of the second oligonucleotide library and comprises a partial sequence complementary to the defined third section of the second oligonucleotide library, at least one second complementary variable codon triplet, a partial sequence complementary to the second partial sequence of the spacer element of the oligonucleotides of the second oligonucleotide library and a subsequently arranged defined 3' overhang;

OR a first oligonucleotide library consisting of oligonucleotides each comprising a partial sequence corresponding to the defined first section of the nucleic acid library, at least one first variable codon triplet and a subsequently arranged first partial sequence of a spacer element;
  a first complementary oligonucleotide which may be a member of a library of first complementary oligonucleotides, each member comprising at least one codon triplet complementary to that of one of the oligonucleotides from the first oligonucleotide library, wherein the first complementary oligonucleotide is complementary to the oligonucleotides of the first oligonucleotide library and comprises a defined 5' overhang, a partial sequence complementary to the first partial sequence of the spacer element of the oligonucleotides of the first oligonucleotide library, at least one first complementary variable codon triplet and a partial sequence complementary to the defined first section of the oligonucleotides of the first oligonucleotide library;
  a second oligonucleotide library consisting of oligonucleotides with a defined 5' overhang comprising a partial sequence forming the second partial sequence of the spacer element, at least one second variable codon triplet and a partial sequence corresponding to the defined third section of the nucleic acid library; and
  a second complementary oligonucleotide which may be a member of a library of second complementary oligonucleotides, each member comprising at least one codon triplet complementary to that of one of the oligonucleotides from the second oligonucleotide library, wherein the second complementary oligonucleotide is complementary to the oligonucleotides of the second oligonucleotide library and comprises a partial sequence complementary to the defined third section of the second oligonucleotide library, at least one second complementary variable codon triplet, and a partial sequence complementary to the second partial sequence of the spacer element of the oligonucleotides of the second oligonucleotide library;

the method comprising:

hybridizing the oligonucleotides of the first oligonucleotide library to the first complementary oligonucleotide to generate a first double-stranded DNA library and hybridizing the oligonucleotides of the second oligonucleotide library to the second complementary oligonucleotide to generate a second double-stranded DNA library;

ligating the first double-stranded DNA library to the second double-stranded DNA library, thereby producing a library of double-stranded DNA ligation products, the library of double-stranded DNA ligation products comprising the following subsections:
a defined first section of the nucleic acid library,
at least one first variable codon triplet,
a spacer element,
at least one second variable codon triplet; and
a third section of the nucleic acid library; and removing the spacer element from the library of double-stranded DNA ligation products, thereby producing a library of double-stranded DNA-product comprising the following subsections:
a defined first section of the nucleic acid library,
at least one first variable codon triplet,
at least one second variable codon triplet; and
a third section of the nucleic acid library.

2. The method of claim 1, wherein each triplet of the at least one first variable codon triplet and the at least one second complementary variable codon triplet consists of three universal-bases or a mixture of all four canonical nucleotides.

3. The method of claim 2, wherein the defined 3' overhangs of the oligonucleotides of the first oligonucleotide library and the second complementary oligonucleotide comprise the same number of nucleotides, wherein the nucleotides are complementary to each other or wherein the defined 5' overhangs of the oligonucleotides of the second oligonucleotide library and the first complementary oligonucleotide comprise the same number of nucleotides, wherein the nucleotides are complementary to each other.

4. The method of claim 3, wherein the oligonucleotides of the first oligonucleotide library and the second complementary oligonucleotide each have defined 3' overhangs that are complementary to each other and wherein the first complementary oligonucleotide and the oligonucleotides of the second oligonucleotide library each have defined 3' overhangs that are each different in length and not complementary to one another and wherein the defined 3' overhangs of the first complementary oligonucleotide and the oligonucleotides of the second oligonucleotide library are each different in length and not complementary to the defined 3' overhangs of the oligonucleotides of the first oligonucleotide library and the second complementary oligonucleotide.

5. The method of claim 3, wherein the oligonucleotides of the second oligonucleotide library and the first complementary oligonucleotide each comprise defined, complementary 5' overhangs and wherein the second complementary oligonucleotide and the oligonucleotides of the first oligonucleotide library each have defined 5' overhangs that are each different in length and not complementary to each other and wherein the defined 5' overhangs of the second complementary oligonucleotide and the oligonucleotides of the first oligonucleotide library are each different in length and not complementary to the defined 5' overhangs of the oligonucleotides of the second oligonucleotide library and the first complementary oligonucleotide.

6. The method of claim 5, wherein the spacer element comprises at least one recognition site for at least one type IIS restriction endonuclease, wherein the least one type IIS restriction endonuclease cuts the double-stranded DNA ligation product 3' after the third nucleotide of the first variable codon triplet and/or 5' in front of the first nucleotide of the second variable codon triplet.

7. The method of claim 6, wherein the first oligonucleotide library comprises two adjoining variable codon triplets or wherein the second oligonucleotide library comprises two adjoining variable codon triplets and wherein the first or the second complementary oligonucleotide each comprises two adjoining complementary variable codon triplets each variable codon triplet consisting of three universal bases or consisting of a mixture of all four canonical nucleotides.

8. The method of claim 7, wherein a nucleic acid sequence of the central second section comprises three or four adjoining variable codon triplets and is produced from the two oligonucleotide libraries and the two oligonucleotides.

9. The method of claim 4, wherein
the ligating step comprises ligating the library of double-stranded DNA ligation product into a suitably prepared cloning vector using the defined 3' overhangs of the first complementary oligonucleotide and of the respective oligonucleotide of the second oligonucleotide library and the corresponding overhangs of the suitably prepared cloning vector, thereby producing a library of ligation product vectors;
the removing step comprises treating the library of ligation product vectors with at least one type IIS restriction endonuclease, wherein the spacer element is excised;
wherein the method further comprises religating and cyclizing the library of cut ligation product vectors thereby producing a library of product vectors with a double-stranded DNA product with the following partial sequences: a first section of the nucleic acid library, at least one first variable codon triplet, at least one second variable codon triplet and a third section of the nucleic acid library.

* * * * *